United States Patent [19]
Sigler et al.

[11] Patent Number: 4,793,809
[45] Date of Patent: Dec. 27, 1988

[54] FIBER FILLED DENTAL PORCELAIN

[75] Inventors: Mark A. Sigler, Kansas City, Kans.; Timothy J. Sigler, St. Joseph; Delbert E. Day, Rolla, both of Mo.

[73] Assignee: Myron International, Inc., Kansas City, Kans.

[21] Appl. No.: 52,843

[22] Filed: May 21, 1987

[51] Int. Cl.$^4$ ............................................. A61C 5/08
[52] U.S. Cl. ................................. 433/218; 433/202.1; 433/212.1; 433/222.1; 433/228.1; 501/17; 501/38
[58] Field of Search ............ 106/35; 433/202.1, 212.1, 433/218, 222.1, 228.1; 501/17, 38

[56] References Cited

U.S. PATENT DOCUMENTS

| 407,145 | 7/1889 | Anderson . | |
|---|---|---|---|
| 407,147 | 7/1889 | Anderson . | |
| 2,533,899 | 12/1950 | Ryner | 25/156 |
| 3,069,773 | 12/1962 | Saffir | 32/8 |
| 3,094,385 | 6/1963 | Brisbin et al. | 23/142 |
| 3,271,173 | 9/1965 | Lockhart et al. | 106/69 |
| 3,381,918 | 5/1983 | Ehrnford | 433/199 |
| 3,503,128 | 3/1970 | Boyd et al. | 32/15 |
| 3,662,405 | 5/1972 | Bortz et al. | 3/1 |
| 3,795,524 | 3/1971 | Sowman | 106/65 |
| 3,865,917 | 2/1975 | Galasso et al. | 264/183 |
| 3,905,047 | 9/1975 | Long | 3/1.9 |
| 3,947,534 | 3/1976 | Mansmann | 264/62 |
| 3,950,478 | 4/1976 | Stuart et al. | 264/234 |
| 3,953,560 | 4/1976 | Klein | 264/50 |
| 4,131,597 | 12/1978 | Bluethgen et al. | 260/42 |
| 4,230,455 | 10/1980 | Hidaka et al. | 433/202 |
| 4,259,072 | 3/1981 | Hirabayaski et al. | 433/173 |
| 4,321,042 | 3/1982 | Scheicher | 433/201 |
| 4,431,451 | 2/1984 | Mabie et al. | 106/35 |
| 4,437,191 | 3/1984 | Zwaag et al. | 3/1 |
| 4,503,157 | 3/1985 | Hatahira | 501/1 |
| 4,516,276 | 5/1985 | Mittelmeier et al. . | |
| 4,543,345 | 9/1985 | Wei | 501/95 |

FOREIGN PATENT DOCUMENTS 61418 9/1976 Australia .

OTHER PUBLICATIONS

McLean, J. W., *The Science and Art of Dental Ceramics*, vol. 1: The Nature of Dental Ceramics and their Clinical Use, pp. 95–98, 105 (1979).
Derand, T., Reinforcement of porcelain crowns with silicon carbide fibers, *The Journal of Prosthetic Dentistry*, vol. 43, No. 1 (Jan. 1980).
Milewski, J. V., Efficient Use of Whiskers in the Reinforcement of Ceramics, *Advanced Ceramic Materials*, vol. 1, No. 1, pp. 36–41 (1986).
Zircar Fibrous Ceramics, Zirconia Bulk Fibers Type ZYBF2, Zircar Products, Inc., Technical Data Bulletin No. ZPI–210 (Nov. 1, 1978).

*Primary Examiner*—Paul Lieberman
*Assistant Examiner*—Linda D. Skaling
*Attorney, Agent, or Firm*—Hovey, Williams, Timmons & Collins

[57] ABSTRACT

Improved dental porcelain compositions and resultant fused porcelain dental restorations are provided which exhibit enhanced strength properties as compared with conventional porcelains. The fiber-filled porcelain compositions of the invention are supplemented with zirconium oxide ceramic fibers in relatively minor amounts of less than 5% by weight. The reinforcing fibers are advantageously predominantly zirconium oxide, and have a relatively short average length of from about 1/32 to ¼ of an inch. These fibers are normally randomly oriented and homogeneously dispersed throughout the fiber-filled porcelain composition, in order to give a reinforcing fiber network. A completed restoration in accordance with the invention would typically include a core portion formed of the fiber filled porcelain, with the outer portion of the restoration being fabricated from conventional non-fiber reinforced porcelain.

8 Claims, No Drawings

4,793,809

FIBER FILLED DENTAL PORCELAIN

BACKGROUND OF THE INVENTION

1. Field of the Invention

The present invention is concerned with improved fiber-reinforced dental porcelain compositions which can be used to good effect in the fabrication of dental restorations such as inlays, onlays, crowns and pontics. More particularly, it is concerned with such reinforced dental porcelains characterized by the presence of relatively minor amounts of zirconium oxide ceramic fibers therein.

2. Description of the Prior Art

Various porcelain ceramics have been used in the past in restorative dentistry, inasmuch as these materials can be used to produce aesthetically pleasing restorations which closely mimic the look and feel of natural teeth. Most dental porcelains are felspar-based, and contain a substantial fraction of silicon dioxide, typically on the order of 50% or more. Apart from $SiO_2$ dental porcelains, porcelains also typically include balancing oxides, fluxes, modifiers and an intermediate, commonly aluminous oxide, $Al_2O_3$. The stability of finished ceramic restorations made from dental porcelains is highly dependent upon the silicon-oxygen lattice developed in the dental glass. As a consequence, covalent bonding within the glass structure must not be reduced significantly, else problems of hydrolytic stability and devitrification may arise.

A persistent problem encountered in connection with dental porcelains is the tendency of the resultant dental restorations to be relatively brittle and subject to breakage. Indeed, this tendency is the prime drawback of all-porcelain restorations. Attempts have been made in the past to strengthen dental porcelain by the inclusion of crystalline oxide powders such as quartz and alumina. Moreover, it has been suggested in the past to employ relatively large quantities of silica-alumina-zirconia refractory glass fibers as an additive in dental porcelains. Thus, U.S. Pat. No. 3,069,773 to Saffir discloses the concept of supplementing dental porcelains with from about 5 to 67% of highly refractory glass fibers including substantial quantities of silica and aluminum, and minor proportions of zirconia. A problem with this approach, however, stems from the fact that such relatively large quantities of reinforcing fiber may tend to reduce the extent of covalent bonding in the silicon-oxygen lattice of the porcelain.

It has further been suggested to employ silicon carbide fibers for the reinforcement of porcelain crowns, Derand, "Reinforcement of Porcelain Crowns with Silicon Carbide Fibers", *J. Pros. Dent.* (January 1980). This technique is of very limited utility, however, inasmuch as the silicon carbide fibers are very dark in color and therefore can be used only in a very small core portion of the restoration, else the aesthetic aspects of the restoration are unacceptable.

In short therefore, the problem of strengthening dental porcelains, while long recognized and the subject of prior research, has remained a troublesome problem which has heretofore not been satisfactorily resolved.

SUMMARY OF THE INVENTION

The present invention overcomes the problems noted above, and provides a greatly improved fiber-reinforced dental porcelain exhibiting enhanced properties of strength and resistance to breakage. Broadly speaking, the porcelain composition of the invention includes a quantity of dental porcelain powder having therein less than 5% by weight of zirconium oxide ceramic fibers, with the fibers having a zirconium oxide content of at least about 50% by weight. It has been found that use of these specialized fibers in relatively moderate amounts produces a finished dental restoration having desirable properties exceeding those of comparative restorations having much higher quantities of zirconium oxide fibers therein.

In preferred forms of the invention, the ceramic fibers are present in the porcelain composition at a level of from about 1 to 4% by weight, and most preferably about 2.5% by weight. The fibers are preferably mixed throughout and randomly oriented in the starting porcelain composition in the fiber-reinforced portion of the final dental restoration. The fibers are normally relatively short, having an average length of from about 1/32 to ¼ of an inch, and more preferably about 1/16 of an inch; however, in certain specialized restorations such as elongated bridge pontics, use can be made of long fibers having a length of one inch or more. In the case of the more usual short fibers though, it is desired that the fibers have a length to diameter ratio of from about 3 to 75, and more preferably from about 7 to 20.

A wide variety of dental porcelains can be used in the context of the invention. Basically speaking, such porcelains include a substantial portion of silicon dioxide, normally at least about 40% by weight, and more usually in excess of 50% by weight. Additionally, the dental porcelain may contain a quantity of $Al_2O_3$, usually from about 5 to 15% by weight, as well as typical fluxes or modifiers (e.g., CaO, $K_2O$, $Na_2O$). These additives are typically present at relatively minor levels. Also, pigments can be used in the dental porcelain compositions in order to give the proper aesthetic appearance to the final dental restorations.

The resultant restorations produced using the fiber-reinforced porcelains of the invention are in the form of a body (e.g., inlays, onlays, crowns and pontics) having a portion thereof (usually the core) formed of fused, fiber-reinforced dental porcelain. In this connection, it is within the ambit of the invention to provide composite restorations having a metallic core and an outer core section of the dental porcelain of the invention. In any event, conventional non-fiber reinforced porcelain is used on the outer surface of the restoration for aesthetic reasons.

As indicated above, in most cases the reinforced fibers are homogeneously dispersed throughout and randomly oriented in the porcelain matrix of the fiber-reinforced core of the finished restoration. This has been found to give increased strength not only in the core but throughout the entire restoration.

DESCRIPTION OF THE PREFERRED EMBODIMENTS

In producing the most preferred fiber-reinforced porcelain composition in accordance with the invention, use is made of dental porcelain commercialized by Myron International, Inc. of Kansas City, Kans. This dental porcelain is but one of a number of such dental porcelains which contain at least about 50% by weight $SiO_2$, together with from about 10 to 20% $Al_2O_3$ and from about 8 to 15% $K_2O$. In addition, such porcelain powder may include minor amounts of CaO, MgO, $LiO_2$, $Na_2O$, $B_2O_3$ and $Fe_2O_3$. Obviously, many variation or other additions known to skilled artisans can be employed in such powders and are within the ambit of the invention.

The zirconium oxide ceramic fibers most preferred for use in the invention are produced and sold by Zircar Products, Inc. of Florida, New York, and are commercialized as "Zirconia Bulk Fibers Type ZYBF2". These fibers are fully described in a technical bulletin distributed by the manufacturer dated Nov. 1, 1978 and bearing number ZPI-210. This product brochure is hereby incorporated by reference herein. Briefly however, these zirconia fibers have high refractoriness, low thermal conductivity and resistance to chemical attack. They are stabilized in the cubic phase with yttria, having a melting pont of 3700° F., and are stable in both oxidizing and reducing conditions. The fibers are relatively short, having a mean length of 1/16 of an inch. The individual zirconia fibers are white in color, have a diameter of 3 to 6 microns, an yttria stabilizer content of 8% by weight, a cubic crystalline phase, and a composition ($ZrO_2 + HfO_2 + Y_2O_3$) of greater than 99%.

Generally speaking, the zirconium oxide fibers useful in the invention should have a content of at least about 50% by weight $ZrO_2$, and more preferably at least about 75% by weight $ZrO_2$. This is to be contrasted with fibers of the type described in U.S. Pat. No. 3,069,773 which are not predominantly zirconia, but typically include rather small percentages of zirconia therein.

It should also be understood that while the term "fibers" is used herein, such should be understood to refer to a wide variety of similar products characterized by exemplary terms such as filaments, whiskers or fibers.

In the production of porcelain powder compositions in accordance with the invention, the desired amount of zirconium oxide fibers is placed in a blender along with the appropriate quantity of conventional dental porcelain. As indicated above, the content of fibers should be less than 5% by weight, preferably about 1–4% by weight, and most preferably about 2.5% by weight. These components are then mixed in the blender for a period of 2 minutes, in order to assure even and random distribution of the fibers throughout the porcelain powder. The fiber-supplemented porcelain can then be packaged for subsequent use or sale.

The most preferred porcelain powders in accordance with the invention are of the medium to high baking or fusing variety, and have maximum bake temperatures of from about 1600° to 2000° F. Use of fibers in accordance with the invention makes it preferable to elevate the final baking temperatures over what would normally be used with the unsupplemented porcelain. Thus, the final porcelain compositions in accordance with the invention would typically be baked to a final temperature of from 20° to 50° F. higher than the nominal maximum baking temperature normally used.

Using the most preferred porcelain and zirconium oxide ceramic fibers described above, the first bake maturing temperatures are increased 20° over the manufacturer's recommendation of 1800° F. As core of fiber is increased, then temperature will change and will generally be increased. Of course, optimum temperatures in each case can be readily determined based upon the particular firing oven being used and technician preference. However, in the use of the most preferred Mirage porcelain having about 2.5% by weight of the described zirconia oxide fibers therein, the following procedure is recommended, assuming that an appropriate refractory model of the involved tooth or teeth has been produced by known methods. The described procedure involves production of an all glass interior bridge and can be readily modified to produce other types of restorations. First, the model is soaked in water for one minute or until bubbles stop, whichever occurs first. The fiber reinforced porcelain mixture is first supplemented with porcelain stiffener in order to enhance the workability of the mixture. Next the fiber porcelain is built to a height of approximately one millimeter short of the final incisal region also keeping the facial surfaces approximately one millimeter recessed to permit placing of finishing porcelain over the fiber reinforced core. When the pontic core obtains the desired form, it is longitudinally sawed to create a ditch. The pontic is then fired in accordance with the procedure set forth in the accompanying table under "First and Second Fiber Buildup." After the initial firing, the model and first buildup of porcelain are soaked in water for one minute or until bubbles stop, whichever occurs first. Additional quantities of fiber reinforced material are placed in the crack or ditch created where the pontic was sawed. The fiber-reinforced material is then built up to form peaks similar to natural dentin, and bulk is added as necessary to extend the pontic core to approximately 1½ to 2 millimeters short of the final contours of the restoration. The second buildup of fiber reinforced porcelain is then fired in accordance with the "First and Second Fiber Buildup" procedures set forth in the accompanying table. After the second firing the pontic core and model are soaked in water for one minute or until bubbles stop, whichever occurs first. Appropriately colored conventional dental porcelain material is applied to the gingival surfaces and along the mesial and distal embrasures, and the doctor's prescribed shade is used as a guide to build the restoration to full contour. The restoration and model are then fired in accordance with the "First Body Buildup" procedure set forth in the accompanying table. A second body buildup is then applied to the restoration. This involves cutting the tissue area from the investment die with a diamond burr to expose the underside of the pontic. The model and pontic are soaked in water for one minute or until bubbles stop, whichever occurs first. Appropriate incisal body and investment porcelain are applied as needed to develop desired aesthetics. The underside of the pontic is checked for flaws and filled in as necessary. The restoration is then fired in accordance with the "Second Body Buildup" procedure in the accompanying table.

Finally, the restoration is finished by conventional means, which may include application of glazing protein and appropriate firing.

Actual experiments using porcelain compositions in accordance with the invention result in finished dental restorations having improved strength characteristics. While the extent of strength supplementation varies depending upon the type of porcelain being used, generally speaking the desired characteristics of the final restoration is decreased when fiber addition is increased above 5% by weight. Certainly, at the 10% level of addition, negative results are typical. Therefore, it is much preferred to use relatively minor amounts of fiber in the compositions hereof, as opposed to the suggestion of major addition as exemplified by the teachings of U.S. Pat. No. 3,069,773.

TABLE

FIRING CYCLES CHART

| | First and Second Fiber Buildup (°F.) | First Body Buildup (°F.) | Second Body Buildup (°F.) |
|---|---|---|---|
| Dry Out Temperature | 935 | 900 | 935 |
| Insertion Temperature | 935 | 900 | 935 |
| Insertion Time | 7 min. | 7 min. | 7 min. |
| Sec. Vacuum Pressure | 26–29 Hg | 26–29 Hg | 26–29 Hg |
| Set Heating Rate | 90 | 75 | 90 |
| Fire Under Vaccum | 935–1700 | 900–1630 | 935–1670 |
| Vacuum Release | −30/1700 | −80/1630 | −30/1670 |
| Fire Under Air to | 1700–1730 | 1630–1710 | 1670–1700 |
| Time at Temperature | 0 | 0 | 0 |
| Removal Time | 2 min. | 2 min. | 2 min. |

We claim:

1. A dental restoration comprising a porcelain body selected from the group consisting of inlays, onlays, crowns and pontics having at least a core portion thereof formed of fused dental porcelain having a total fiber content of from about 1 to 4% by weight based upon the weight of the core portion and dispersed in the core portion, at least 25% by weight of said total fiber content being zirconium oxide ceramic fibers having a zirconium oxide content of at least about 50% by weight, said dental restoration further including an outer portion disposed about said core portion and being formed of non-fiber filled dental porcelain, the dental porcelain making up said core and outer portions including a major amount of $SiO_2$, and respective smaller quantities of $Al_2O_3$ and $K_2O$.

2. The restoration of claim 1, said fibers being homogeneously dispersed throughout and randomly oriented in said fiber-containing dental porcelain.

3. The restoration of claim 1, said ceramic fibers being white or essentially colorless in said composition.

4. The restoration of claim 1, said fibers having an average length of from about 1/32 to ¼ inch.

5. lThe restoration of claim 4, said fibers having an average length of about 1/16 of an inch.

6. The restoration of claim 1, said fibers having an average length to diameter ratio of from about 3 to 75.

7. The restoration of claim 6, said average length to diameter being from about 7 to 20.

8. The restoration of claim 1, said dental porcelain making up said core portion including at least about 5% of aluminous oxide therein.

* * * * *